(12) United States Patent
Merkel et al.

(10) Patent No.: US 8,258,355 B2
(45) Date of Patent: Sep. 4, 2012

(54) PROCESSES FOR PREPARING 1,1,2,3-TETRACHLOROPROPENE

(75) Inventors: Daniel C. Merkel, West Seneca, NY (US); Hsueh S. Tung, Getzville, NY (US); Michael Van Der Puy, Amherst, NY (US); Jing Ji Ma, Skokie, IL (US)

(73) Assignee: Honeywell International Inc., Morristown, NJ (US)

( * ) Notice: Subject to any disclaimer, the term of this patent is extended or adjusted under 35 U.S.C. 154(b) by 291 days.

(21) Appl. No.: 12/178,984

(22) Filed: Jul. 24, 2008

(65) Prior Publication Data

US 2009/0030249 A1    Jan. 29, 2009

Related U.S. Application Data

(60) Provisional application No. 60/951,774, filed on Jul. 25, 2007.

(51) Int. Cl.
*C07C 17/25* (2006.01)
(52) U.S. Cl. ......... 570/229; 570/226; 570/227; 570/228
(58) Field of Classification Search .................. None
See application file for complete search history.

(56) References Cited

U.S. PATENT DOCUMENTS

| 3,823,195 | A | | 7/1974 | Smith |
| 4,535,194 | A | | 8/1985 | Woodard |
| 4,650,914 | A | * | 3/1987 | Woodard ............. 570/236 |
| 5,202,102 | A | * | 4/1993 | Nguyen ............. 423/240 S |
| 5,821,394 | A | * | 10/1998 | Schoebrechts et al. ....... 570/227 |
| 2005/0090698 | A1 | * | 4/2005 | Merkel et al. .............. 570/155 |
| 2007/0197842 | A1 | | 8/2007 | Mukhopadhyay |

FOREIGN PATENT DOCUMENTS

JP    06228029 A  *  8/1994

OTHER PUBLICATIONS

S. Shavanov et al., E.V. USSR, Khimicheskaya Promyshlennost, Moscow, Russian Federation, 1987, (2), 79-81.

\* cited by examiner

*Primary Examiner* — Sudhakar Katakam
(74) *Attorney, Agent, or Firm* — Bruce O. Bradford

(57) ABSTRACT

Provided is a continuous process for preparing 1,1,2,3-tetrachloro-1-propene having the steps of catalytically dehydrochlorinating $CH_2ClCCl_2CH_2Cl$ in the gas phase to produce $CHCl{=}CClCH_2Cl$; chlorinating the $CHCl{=}CClCH_2Cl$ to form $CHCl_2CCl_2CH_2Cl$; and catalytically dehydrochlorinating the $CHCl_2CCl_2CH_2Cl$ in the gas phase to form $CCl_2{=}CClCH_2Cl$.

19 Claims, No Drawings

PROCESSES FOR PREPARING 1,1,2,3-TETRACHLOROPROPENE

CROSS-REFERENCE TO RELATED APPLICATION

This application claims the priority benefit of U.S. Provisional Application No. 60/951,774, filed Jul. 25, 2007, which is incorporated herein by reference.

FIELD OF THE INVENTION

The present invention relates to methods for preparing chlorinated olefins. More specifically, preferred embodiments of the present invention concern processes for preparing chlorinated propene, more particularly 1,1,2,3-tetrachloropropene, $CH_2Cl-CCl=CCl_2$, (HCO-1230).

BACKGROUND OF THE INVENTION

Recently, the use of compositions comprising tetrafluoropropenes have been disclosed as a refrigerant and as a blowing agent, among other uses, with advantageous characteristics, such as low global warming potential, low toxicity, and low ozone depletion potential.

One process for producing tetrafluoropropenes involves the use of tetrachloropropenes as a reactant. (See, e.g., US 2007-0197842 A1). As a result, applicants have come to recognize a need for improved methods for producing certain tetrachloropropenes.

Several processes for making tetrachloropropenes such as $CCl_3CCl=CH_2$ and $CCl_2=CClCH_2Cl$ are known. Conventional starting materials include allyl chloride and 1,2,3-trichloropropane, the latter being formed upon chlorination of the former. Starting from 1,2,3-trichloropropane, a repetitive series of dehydrochlorinations and chlorinations with elemental chlorine follow until the desired number of chlorine atoms have been added (Shavanov, S. S.; Tolstikov, G. A.; Shutenkova, T. V.; Ryabova, N. A.; Shurupov, E. V. USSR. Khimicheskaya Promyshlennost (Moscow, Russian Federation) (1987), (2), 79-81).

Dehydrochlorinations are usually conducted with an aqueous base, such as aqueous NaOH, in the presence of a phase transfer catalyst, such as quaternary ammonium salts. The phase transfer catalysts not only improve the rate compared to aqueous NaOH alone, but also help maintain high selectivity at a high conversion. Nonetheless, such processes are not entirely ideal due to the potential environmental hazards associated with quaternary ammonium salts. In addition, after each of the reaction steps involving aqueous base, a drying step and/or waste treatment of the aqueous solution may be required, which adds to the cost and time required to conduct the manufacturing operation. Also, the current invention allows for recovery of the hydrochloric acid co-product, if so desired.

Another general method is the chlorination of chlorinated alkanes having fewer chlorine atoms than desired in the final product. This process, which involves hydrogen substitution by chlorine, can reduce the number of process steps required to achieve the desired number of chlorine substitutions. However, these processes frequently suffer from a lack of selectivity. As a consequence, both un-chlorinated and over-chlorinated materials are produced in addition to an array of isomers.

With respect to the tetrachloropropenes, the isomers $CCl_3CCl=CH_2$ and $CCl_2=CClCH_2Cl$ are in some instances equivalent in terms of chemical transformations, but the former is thermodynamically unstable relative to the latter. Since the isomerization of the former is exothermic to the latter, storage and shipping of the $CCl_3CCl=CH_2$ presents a potential hazard. Thus there is a need for a process of making $CCl_2=CClCH_2Cl$ which has high selectivity for this particular isomer and which does not suffer from the other limitations already noted.

All the steps of the process described in the current invention can be run in a continuous mode which is economically advantages over its predecessors which appear to be a combination of continuous and batch mode steps.

DETAILED DESCRIPTION OF PREFERRED EMBODIMENTS

Applicants have developed an improved process for the synthesis of $CCl_2=CClCH_2Cl$. In certain embodiments, the process of the present invention comprises the steps of:
a) dehydrochlorinating $CH_2ClCCl_2CH_2Cl$ in the presence of a non-aqueous catalyst to produce a product comprising $CHCl=CClCH_2Cl$;
b) chlorinating at least a portion of the $CHCl=CClCH_2Cl$ from step (a) to form a product comprising $CHCl_2CCl_2CH_2Cl$; and
c) dehydrochlorinating at least a portion of the $CHCl_2CCl_2CH_2Cl$ from step (b) in the presence of a non-aqueous catalyst to form a product comprising $CCl_2=CClCH_2Cl$.

In another embodiment, the starting material, $CH_2ClCCl_2CH_2Cl$, is prepared from 2,3-dichloropropene, which in turn is prepared from allyl chloride using a combination of chlorine additions and non-aqueous, catalytic dehydrochlorinations. Preferred steps of this process are outlined below:

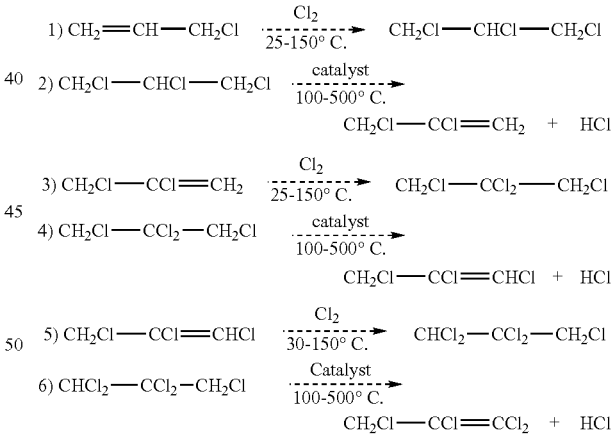

In certain preferred embodiments, reaction steps 2), 4), and 6) are run in a continuous mode. In certain embodiments, reaction steps 1), 3), and 5) are run in batch mode. In certain other embodiments, one or more of steps 1), 3), and 5) are run in continuous mode.

The preferred catalysts for the preferred dehydrochlorination steps of the present methods, for example steps 2, 4, and 6 in the particular scheme disclosed above, comprise, and preferably in major proportion on the basis of total active catalyst, one or more halogenated metal oxides, and/or one or more Lewis acid metal halides, one or more zero valent metals, and/or activated carbon. In preferred embodiments, the catalyst is selected from the group consisting of: 1) halogenated transition metal oxides and their mixtures including all the transition metals plus $Li^+$, $Na^+$, $K^+$, $Mg^+$, $Cs^+$, $Ce^{+4}$, $Ce^{+3}$, $Al^{+3}$, and $La^{+3}$; 2) Lewis acid metal halides and their mixtures including all the transition metal plus $Li^+$, $Na^+$, $K^+$, $Mg^+$, $Cs^+$, $Ce^{+4}$, $Al^{+3}$, and $La^{+3}$; 3) zero valent metals, metal alloys and their mixtures; 4) pre-treated activated carbons; and 5) combinations of these. Particularly useful halogenated transition metal oxides include, but are not limited to, $Cr_2O_3$, $Fe_2O_3$, $Al_2O_3$, $NiO_2$, $MoO_3$, $WO_3$, $TiO_2$, $V_2O_5$, MgO and combinations of these. Particularly useful Lewis acid metal halides include, but are not limited to, $AlCl_3$, $AlF_3$, $FeCl_3$, $CrF_3$, LiF, NaF, KF, CsF, $MgCl_2$, $MgF_2$, $CaF_2$, LiCl, NaCl, KCl, and CsCl and combinations of these. Particularly useful zero valent metals include, but are not limited to, Pd, Pt, Rh, Fe, Co, Ni, Cu, Mo, Cr, and Mn, and combinations of these. The catalyst may be supported or unsupported. Useful examples of metal alloys include, but are not limited to, SS 316, Monel 400, Inconel 825, Inconel 600, and Inconel 625. Activated carbon treatment methods preferably comprise mixing the activated carbon with an acid, an oxidizing agent in a liquid phase, or an oxidizing agent in a gas phase. Activated carbons undergoing one or more of these methods can exhibit improved stability during the dehydrochlorination process.

All the catalysts for use in connection with the present invention can be bulk or supported on a substrate such as activated carbon, graphite, silica, alumina, zeolites, fluorinated graphite, and fluorinated alumina.

EXAMPLES

Example 1

Synthesis of $CH_2ClCHClCH_2Cl$ from $Cl_2$ and $CH_2ClCH=CH_2$

A 250 mL three-necked flask is equipped with stir bar, thermometer, reflux condenser cooling with −50° C. cooling fluid, and $Cl_2$ inlet which is connected to a flow meter and then a $Cl_2$ feed cylinder. The top of the condenser is connected to a scrubber to treat any un-reacted $Cl_2$. The reactor is heated in an oil bath to control inside temperature to about 45° C.-50° C. About 100 g of $CH_2=CHCH_2Cl$ is added to the flask, and then $Cl_2$ is bubbled into the $CH_2=CHCH_2Cl$ at a rate of about 5 to about 10 grams per hour while the mixture is continuously stirred. The progress of the reaction is monitored by gas chromatography. Chlorination is continued until the conversion of $CH_2=CHCH_2Cl$ is about 95% or greater, and the major component in the reaction product is $CH_2ClCHClCH_2Cl$, which is preferably present in an amount of at least about 90 mole % of the reaction product.

Example 2

Synthesis of $CH_2ClCCl=CH_2$ from $CH_2Cl—CHClCH_2Cl$

A ½" OD×36" long reaction tube is prepared by charging the tube with about 65 cc of $Cr_2O_3$ catalyst. A thermocouple is inserted into the center of the catalyst bed to monitor reaction temperatures. A coiled section of 10 ft length of ¼" OD monel tube is connected to the reactor inlet and serves as a vaporizer/superheater for the organic feed that is being introduced. The vaporizer and reaction tube are heated by a sand bath until the catalyst bed temperature is about 350° C. $CH_2ClCHClCH_2Cl$, preferably as produced by the reaction product of Example 1, is fed (preferably via a peristaltic pump) at a rate of about 9 to about 10 grams per hour. Product is collected in a cold trap (product collection cylinder) for a total of about 2 hours. The organic recovered is analyzed using GC. The GC results show about 90% or greater conversion of $CH_2ClCHClCH_2Cl$. The major product is $CH_2ClCCl=CH_2$, preferably being present in the reaction product in an amount that is about 95 mole % or greater of the reaction product.

Example 3

Synthesis of $CH_2ClCCl_2CH_2Cl$ from $CH_2ClCCl=CH_2$ and $Cl_2$

The same reaction apparatus as in Example 1 is used. The reactor is heated in an oil bath to control the inside temperature of from about 45° C. to about 50° C. About 100 g of $CH_2ClCCl=CH_2$ is added to the flask. Chlorine is bubbled into the $CH_2ClCCl=CH_2$ at a 5-10 grams per hour. The reaction is allowed to proceed until a 85% or greater conversion of $CH_2Cl—CCl=CH_2$ is achieved, and the major product is $CH_2ClCCl_2CH_2Cl$, which in preferred embodiments is present in the reaction product in amounts of from about 85 mole % or greater.

Example 4

Synthesis of $CH_2ClCCl=CHCl$ from $CH_2ClCCl_2CH_2Cl$

The same reaction apparatus and catalyst as in Example 2 is used. The vaporizer and reaction tube are heated to a temperature of about 350° C. $CH_2ClCCl_2CH_2Cl$ is fed via a peristaltic pump at a rate of about 9 to about 10 grams per hour. After 2 hours the organic collected in the cold trap is analyzed using a GC. The GC results show a conversion of about 90% or greater of $CH_2ClCCl_2CH_2Cl$. The major reaction product is $CH_2ClCCl=CHCl$, which is preferably present in the reaction product in an amount that is at least about 80 mole %.

Example 5

Synthesis of $CH_2ClCCl_2CH_2Cl$ from $CH_2ClCCl=CHCl$ and $Cl_2$

The same reaction apparatus as in Example 1 is used. The reactor is heated in an oil bath to control the inside temperature of from about 30° C. to about 35° C. About 100 g of $CH_2ClCCl=CHCl$ is added to the flask. Chlorine is bubbled into the $CH_2ClCCl=CHCl$ at 5-10 grams per hour while the mixture is continuously stirred. The reaction is continued to a conversion of $CH_2ClCCl=CHCl$ of about 85% or greater, and the major product is $CHCl_2CCl_2CH_2Cl$, which in preferred embodiments is present in the reaction product in amounts of from about 85 mole % or greater.

Example 6

Synthesis of $CH_2ClCCl=CCl_2$ from $CHCl_2CCl_2CH_2Cl$

The same reaction apparatus as in Example 2 is used, except that the reactor is charged with 65 cc of activated carbon catalyst. The vaporizer and reaction tube are heated to a temperature of about 250° C. $CHCl_2CCl_2CH_2Cl$ is fed via a peristaltic pump at a rate of about 9 to about 10 grams per hour. Product is collected in a cold trap (product collection cylinder) for a total of 2 hours. The organic recovered is analyzed using GC. The GC results show a conversion of about 90% or greater of $CHCl_2CCl_2CH_2Cl$. The major reaction product is $CH_2ClCCl=CCl_2$, which is preferably present in the reaction product in an amount that is at least about 80 mole %.

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A process for preparing 1,1,2,3-tetrachloro-1-propene comprising:
chlorinating $CH_2=CHCH_2Cl$ in the presence of $Cl_2$ gas to form a first precursor product comprising $CH_2ClCHClCH_2Cl$, wherein the selectivity for $CH_2ClCHClCH_2Cl$ is at least about 90%;
catalytically dehydrochlorinating at least a portion of the $CH_2ClCHClCH_2Cl$ of said first precursor product to form a second precursor product comprising $CH_2ClCCl=CH_2$;
chlorinating at least a portion of said $CH_2ClCCl=CH_2$ in the presence of $Cl_2$ gas to form a third precursor product comprising $CH_2ClCCl_2CH_2Cl$;
dehydrochlorinating in the vapor phase at least a portion of said $CH_2ClCCl_2CH_2Cl$ and in the presence of a first catalyst to produce a first intermediate product comprising $CHCl=CClCH_2Cl$;
chlorinating at least a portion of the $CHCl=CClCH_2Cl$ of said first intermediate product to form a second intermediate product comprising $CHCl_2CCl_2CH_2Cl$; and
dehydrochlorinating at least a portion of the $CHCl_2CCl_2CH_2Cl$ from said second intermediate product in the vapor phase and in the presence of a second catalyst to form a final product comprising $CCl_2=CClCH_2Cl$.

2. The process of claim 1 wherein said final product comprises a majority portion of $CCl_2=CClCH_2Cl$ relative to other tetrachloropropene isomers present in said final product.

3. The process of claim 2 wherein said first and second catalysts are selected from the group consisting of halogenated transition metal oxides and their mixtures, Lewis acid metal halides and their mixtures, zero valent metals, metal alloys and their mixtures, pre-treated activated carbons, and combinations of these.

4. The process of claim 3 wherein at least one of said first and second catalysts is a halogenated transition metal oxide or at least one metal oxide selected from the group consisting of $Li^+$, $Na^+$, $K^+$, $Mg^+$, $Cs^+$, $Ce^{+4}$, $Ce^{+3}$, $Al^{+3}$, and $La^{+3}$.

5. The process of claim 4 wherein said halogenated transition metal oxide contains a transition metal oxide selected from the group consisting of $Cr_2O_3$, $Fe_2O_3$, $Al_2O_3$, $NiO_2$, $MoO_3$, $WO_3$, $TiO_2$, $V_2O_5$, and $MgO$.

6. The process of claim 3 wherein at least one of said first and second catalysts is a Lewis acid metal halide or at least one Lewis acid metal halide selected from the group consisting of $Li^+$, $Na^+$, $K^+$, $Mg^+$, $Cs^+$, $Ce^{+4}$, $Al^{+3}$, and $La^{+3}$.

7. The process of claim 6 wherein said Lewis acid metal halide is selected from the group consisting of $AlCl_3$, $AlF_3$, $FeCl_3$, $CrF_3$, $LiF$, $NaF$, $KF$, $CsF$, $MgCl_2$, $MgF_2$, $CaF_2$, $LiCl$, $NaCl$, $KCl$, and $CsCl$.

8. The process of claim 3 wherein at least one of said first and second catalysts is a zero valent metal or alloy.

9. The process of claim 8 wherein said zero valent metal or alloy comprises a metal selected from the group consisting of Pd, Pt, Rh, Fe, Co, Ni, Cu, Mo, Cr, and Mn.

10. The process of claim 3 wherein at least one of said first and second catalysts is pretreated activated carbon.

11. The process of claim 3 wherein said first and second catalysts are unsupported.

12. The process of claim 3 wherein at least one of said first and second catalysts are supported.

13. The process of claim 3 wherein said first and second catalysts are supported.

14. The process of claim 1 wherein said dehydrochlorinating $CH_2ClCCl_2CH_2Cl$ and dehydrochlorinating $CHCl_2CCl_2CH_2Cl$ are preformed in a continuous mode.

15. The process of claim 1 wherein said dehydrochlorinating $CH_2ClCCl_2CH_2Cl$ and dehydrochlorinating at least a portion of the $CHCl_2CCl_2CH_2Cl$ are independently performed at a temperature of about 100 to about 500° C.

16. The process of claim 1 wherein said chlorinating at least a portion of the $CHCl=CClCH_2Cl$ is performed at a temperature of about 30 to about 150° C.

17. The process of claim 1 wherein said dehydrochlorinating $CH_2ClCHClCH_2Cl$ is preformed in a continuous mode.

18. The process of claim 1 wherein the conversion of $CH_2ClCCl_2CH_2Cl$ to $CH_2ClCCl=CHCl$ is about 90% or greater.

19. The process of claim 1 wherein the conversion of $CHCl_2CCl_2CH_2Cl$ to $CCl_2=CClCH_2Cl$ is about 90% or greater.

* * * * *